United States Patent [19]

Ichimura

[11] 4,272,620

[45] Jun. 9, 1981

[54] POLYVINYL ALCOHOL-STYRYLPYRIDINIUM PHOTOSENSITIVE RESINS AND METHOD FOR MANUFACTURE THEREOF

[75] Inventor: Kunihiro Ichimura, Yokohama, Japan

[73] Assignees: Agency of Industrial Science and Technology; Ministry of International Trade & Industry, both of Tokyo, Japan

[21] Appl. No.: 62,490

[22] Filed: Jul. 31, 1979

[30] Foreign Application Priority Data

Aug. 9, 1978 [JP] Japan ................................. 53/96803
Nov. 6, 1978 [JP] Japan ................................. 53/136536

[51] Int. Cl.$^3$ ............................................. C08F 8/44
[52] U.S. Cl. .................................... 525/61; 428/461; 428/463; 430/287; 542/422

[58] Field of Search ........................................ 525/61

[56] References Cited

PUBLICATIONS

Makromol Chem., 73, 203–214, (1964).
Pure & Appl. Chem., 49, 523–538, (1977).
Chemistry Letters, 1289–1292, (1978).

*Primary Examiner*—Stanford M. Levin
*Attorney, Agent, or Firm*—Oblon, Fisher, Spivak, McClelland & Maier

[57] ABSTRACT

A hydrophilic resin comprising a polyvinyl alcohol polymeric backbone and containing styrylpyridinium groups is a photosensitive resin. The photosensitive resin is prepared by reacting a styrylpyridinium salt containing a formyl or acetal group with a polyvinyl alcohol compound.

10 Claims, No Drawings

POLYVINYL ALCOHOL-STYRYLPYRIDINIUM PHOTOSENSITIVE RESINS AND METHOD FOR MANUFACTURE THEREOF

BACKGROUND OF THE INVENTION:

This invention relates to a photosensitive resin of high solubility in water and high sensitivity and to a method for the manufacture of this resin.

Photosensitive resins have been used as raw materials for printing plates, as photoresists for photo etching and photomilling operations and as photosensitive vehicles for paints and printing inks. In recent years, studies have been conducted on the use of these resins for the immobilization of enzymes.

The photosensitive resins which have been known are those having azide group, cinnamoyl group, acryloyl group, etc. as their photosensitive residues. As immobilizing carriers for enzymes, however, these conventional photosensitive resins are not considered to be satisfactory because they have serious problems such as the adverse effects they bring about on enzymes and the solubility they exhibit in water.

As a photosensitive high-molecular compound suitable for such new uses, the inventors formerly synthesized polymers possessing a styrylpyridinium group by the reaction of styrylpyridiniums with the polymer of 2-chloroethyl vinyl ether and demonstrated this polymer to be suitable for the photo-immobilization of enzymes [Ichimura and Watanabe: Collection of Manuscripts II for the 37th Spring Annual Meeting of the Japan Chemical Society, page 1133 (1978) and Chemistry Letters, page 1289 (1978)].

The inventors continued an advanced study with a view to further improving the photosensitivity of this polymer. As a result, they have ascertained that the desired improvement is attained by causing a polyvinyl alcohol to incorporate therein a styrylpyridinium group. The present invention has issued from this knowledge.

An object of this invention is to provide a novel photosensitive resin which possesses high solubility in water and high sensitivity and, therefore, is suitable as a photoresist and a photosensitive vehicle and also as an immobilizing carrier for enzymes.

Another object of this invention is to provide a method for the manufacture of the novel photosensitive resin described above.

SUMMARY OF THE INVENTION

To accomplish the objects described above according to the present invention, there is provided a photosensitive resin which comprises a polyvinyl alcohol derivative having incorporated therein a photosensitive group of the generic formula:

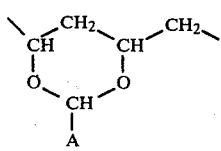

wherein, A represents either
(1) a group of the generic formula:

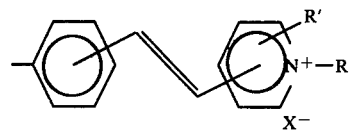

wherein, R represents one member selected from the class consisting of a hydrogen atom, alkyl groups and lower hydroxyalkyl groups, R' one member selected from the class consisting of a hydrogen atom and alkyl groups and $X^-$ a strongly acidic ion, or (2) a group of the generic formula:

wherein, $R_1$ represents one member selected from the class consisting of a hydrogen atom, alkyl groups and aralkyl groups, $R_2$ one member selected from the class consisting of a hydrogen atom and alkyl groups, n an integer having a value between 1 to 6 inclusive and $X^-$ a strongly acidic ion.

The photosensitive resin described above is produced by causing a styrylpyridinium salt possessing either a formyl group or an acetal group to react upon a polyvinyl alcohol or a partially saponified polyvinyl acetate.

DETAILED DESCRIPTION OF THE PREFERRED EMBODIMENTS

The photosensitive resin of the present invention has a chemical structure formed of a polyvinyl alcohol derivative having incorporated therein a photosensitive group of the following generic formula.

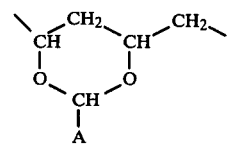

wherein, A represents either a group of the generic formula

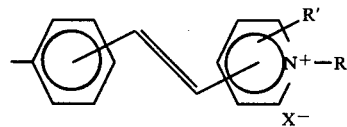

or a group of the generic formula

where, R represents one member selected from the class consisting of a hydrogen atom, alkyl groups and lower hydroxyalkyl groups, R' one member selected from the class consisting of a hydrogen atom and alkyl groups, $R_1$ one member selected from the class consisting of a hydrogen atom, alkyl groups and aralkyl groups, $R_2$ one member selected from the class consisting of a hydrogen atom and alkyl groups, $X^-$ a strongly acidic ion and n an integer having a value between 1 and 6 inclusive.

Hereinafter, the generic formula:

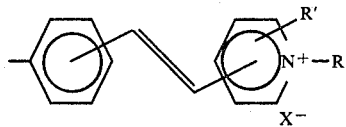

will be denoted as S and the generic formula:

The words "polyvinyl alcohol derivative" as used in the present specification shall mean polyvinyl alcohols and partially saponified polyvinyl acetates and, thus also embraces mixture containing the polymers of both vinyl alcohol and vinyl acetate.

The photosensitive resin of the present invention, therefore, has as its essential constituent units, the aforementioned photosensitive group and the group constituting the aforementioned polyvinyl alcohol derivative. The ratio of these constituent units, specifically the ratio (molar) of the photosensitive group unit to the vinyl alcohol group unit or vinyl acetate group unit is desired to fall in the range of from 0.5:99.5 to 10:90. Although the photosensitive group in the photosensitive resin possesses hydrophilicity in itself, the resin loses its solubility in water when the photosensitive group unit is present in excess of the upper limit. The proportion of the photosensitive group unit present in the resin, however, can be raised past the upper limit when a polar solvent such as an aqueous alcohol, dimethylformamide, formamide or dimethylsulfoxide or a mixed solvent consisting of such a polar solvent and water is used as the solvent.

The photosensitive resin of the present invention is a novel photocrosslinkable substance which exhibits high solubility in water and high sensitivity. In an aqueous solution, the photosensitive resin shows the absorption maximum in the ultraviolet spectrum in the neighborhood of 340 nm where the photosensitive group S is used or 360 nm where the photosensitive group T is used. This resin is insolubilized on exposure to a light having a wavelength of up to 460 nm in the former case or up to 500 nm in the latter case.

The photosensitive resin of the present invention can be produced by reacting a polyvinyl alcohol or a partially saponified polyvinyl acetate with a styrylpyridinium salt possessing a formyl group of the generic formula:

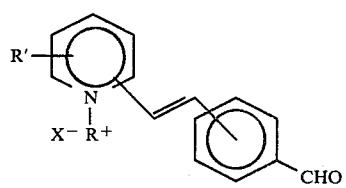

(wherein, R, R' and $X^-$ are as defined above) or a styrylpyridinium salt possessing an acetal group of the generic formula:

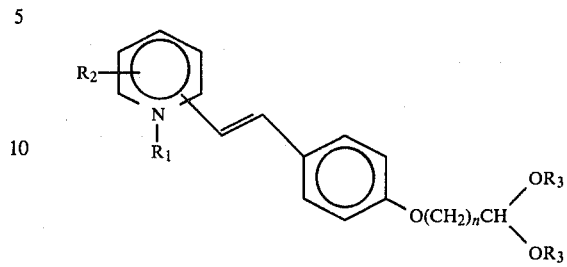

(wherein, $R_1$, $R_2$, n and $X^-$ are as defined above and the two $R_3$'s each represent an alkyl group or a phenyl group or, in a combined form, represent one alkenyl group).

The styrylpyridinium salt to be used as the raw material for the photosensitive resin of this invention is a novel compound. Examples of such styrylpyridinium salts possessing a formyl group include α-(p-formylstyryl)-pyridinium, γ-(p-formylstyryl)-pyridinium, α-(m-formylstyryl)-pyridinium, N-methyl-α-(p-formylstyryl)-pyridinium, N-methyl-β-(p-formylstyryl)-pyridinium, N-methyl-α-(m-formylstyryl)-pyridinium, N-methyl-α-(o-formylstyryl)-pyridinium, N-ethyl-α-(p-formylstyryl)-pyridinium, N-(2-hydroxyethyl)-α-(p-formylstyryl)-pyridinium, N-(2-hydroxyethyl)-γ-(p-formylstyryl)-pyridinium, N-allyl-α-(p-formylstyryl)-pyridinium, N-methyl-γ-(p-formylstyryl)-pyridinium, N-methyl-γ-(m-formylstyryl)-pyridinium, N-benzyl-α-(p-formylstyryl)-pyridinium, N-benzyl-γ-(p-formylstyryl)-pyridinium and N-carbamoylmethyl-γ-(p-formylstyryl)-pyridinium. These quaternary salts may be present in the form of hydrochlorides, hydrobromides, hydroiodides, perchlorates, tetrafluoroborates, methosulfates, phosphates, sulfates, methanesulfonates and p-toluene-sulfonates. These compounds are obtained by subjecting the corresponding picolines or N-alkylpicolinium salts to the condensation with aromatic dialdehydes or formyl-benzaldehydes, and they are used in the form of formylstyrylpyridine salts or quaternized salts.

Examples of the styrylpyridinium salts possessing an acetal group include those listed below.

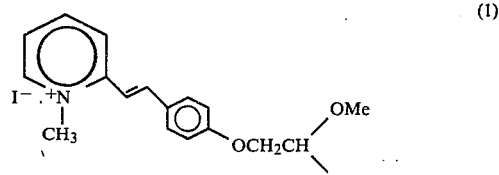

(1)

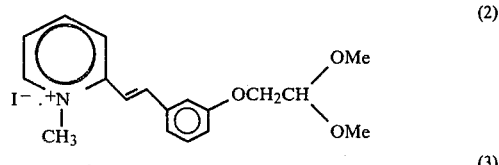

(2)

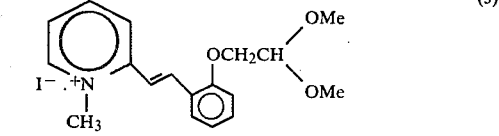

(3)

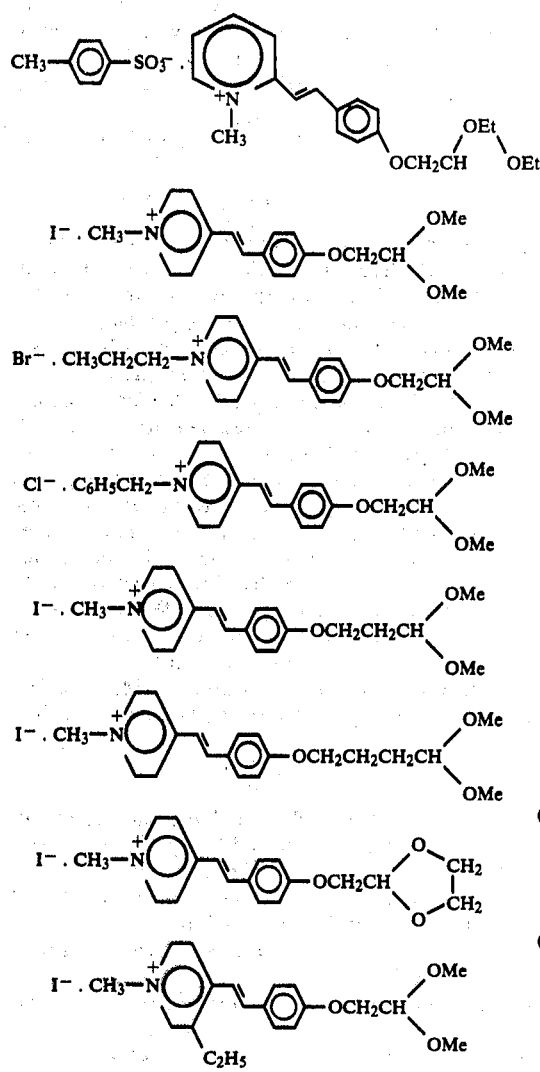

These compounds are obtained by subjecting the corresponding N-alkyl-picolinium salts to the condensation with formylphenoxyacetal.

The polyvinyl alcohol may partly contain an unsaponified acetyl group. This partial inclusion of the group rather meets the purpose of particularly enhancing the solubility of the resin in water. The content of this group is desired not to exceed about 30 mol%. This means that the saponification ratio is desired to be not less than 70%. The degree of polymerization is advantageous in the range of from 400 to 3,000. When the polymerization degree is too small, the time of exposure required for the insolubilization of the resin is notably lengthened. When the polymerization degree is too large, the viscosity is increased even to a point where the actual use of resin is impeded.

The high-polymer acetalization reaction, i.e. the aforementioned reaction of the polyvinyl alcohol or partially saponified polyvinyl acetate upon the styrylpyridinium salt possessing a formyl group, or the high-polymer interacetalization reaction, i.e. the aforementioned reaction of the polyvinyl alcohol or partially saponified polyvinyl acetate upon the styrylpyridinium salt possessing an acetal group, can be advantageously catalyzed with an acid in water as the medium. In this reaction, the amount of the styrylpyridinium salt to be used is desired to be such that the proportion of this salt relative to the vinyl alcohol unit of the polyvinyl alcohol or partially saponified polyvinyl acetate falls in the range of from 0.3 to 20 mol%. As the catalyst for this reaction, any of inorganic and organic acids may be used. Examples of such acids include hydrochloric acid, sulfuric acid, phosphoric acid, perchloric acid, hydroborofluoric acid, methane-sulfonic acid and p-toluene-sulfonic acid. Since the reaction time decreases with the increasing amount of the acid thus added for catalysis, it is desirable to increase the amount of the acid as much as permissible. For practical purposes, however, the amount of the added acid generally suffices in the range of from 0.01 to 5 normalities. The reaction is carried out at temperatures in the range of from room temperature to 100° C. The reaction time is sufficient in the range of from one to 24 hours in the former reaction and in the range of from one to 48 hours in the latter reaction.

In this reaction, the optimum polyvinyl alcohol derivative concentration in the reaction is in the range of from 2 to 20 W/W%.

The progress of the polymer reactions can be traced by precipitating the polymer in alcohol and determining the absorbance due to the styrylpyridinium group in the neighborhood of 340 nm.

The reaction solutions increase photosensitivity as the reaction proceeds. The progress of this reaction, therefore, can easily be traced measuring the degree of photosensitivity of the reaction solution.

In either case, the solution obtained on completion of the reaction can be used, without purification as a photosensitive liquid of high sensitivity. Desired purification of the resin is accomplished after completion of the reaction by pouring the resultant reaction mixture into a large volume of a non-solvent such as acetone, ethanol or dioxane or a coagulation bath containing such substance as sodium sulfate or potassium sulfate and thereby precipitating the photosensitive resin, separating the precipitated resin from a solvent or a bath and washing the separated resin with alcohol. Thorough removal of the trace of the acid used as the catalyst is attained by washing the resin with alcohol containing a small amount of ammonia or giving the resin repeated reprecipitation.

The photosensitve resin of this invention which contains the photosensitive group S is soluble in water and exhibits high sensitivity. It has a sensitivity equal to or some tens of times as high as that of polyvinyl cinnamate sensitized with 5-nitro-acenaphthene. No other resin has been heretofore known to acquire amply high photosensitivity as the result of the incorporation of a photosensitive group in a very low proportion without use of any additional sensitizer. The resin of the present invention proves to be quite economic because it effectively functions with a very small content of the photosensitive group.

In the case of the resin of this invention which contains the photosensitive group T, the absorption zone expands in the direction of increasing wavelength and comes to exhibit increased sensitivity because the oxy group is directly linked and conjugated with the styrylpyridinium group. This resin has the sensitivity equal to or ten-odd times as high as that of polyvinyl cinnamate sensitized with 5-nitroacenaphthene. The photosensitive group need be present in the resin only in extremely low amounts in the neighborhood of 1 mol% and, the resin is characterized by acquiring amply high photosensitivity without use of any additional sensitizer. The sensitivity of the resin is not affected at all by temperature; virtually no difference is found between that at 80° C. and that at −76° C., for example.

By suitable adaptation of the characteristic properties described above, the photosensitive resins of the present invention can be made useful as photoresists, photomilling agents and other printing stocks, as bases for water paints and as vehicles for printing inks. Further, because the points of crosslinking are attained through dimerization of styrylpyridinium groups and, therefore, the crosslinking reaction proceeds in a specific manner in the resin, this resin proves to be highly useful as an immobilizing carrier for biofunctional materials such as enzymes, sectioned live cells and microorganisms. In view of the adhesive strength inherent in its polyvinyl alcohol unit, the resins also prove to be useful as adhesives and binders of the type allowed to manifest their latent properties in an enhanced manner upon exposure to light.

Now, the present invention will be described more specifically by reference to working examples thereof. Examples 1-6 concern raw materials for the resins of the present invention and Examples 7-24 the resins of the invention.

EXAMPLE 1

In a mixed solution consisting of 22.4 g of acetic anhydride and 12.0 g of glacial acetic acid, 18.6 g of α-picoline and 33.5 g of terephthal dialdehyde were dissolved and refluxed under application of heat for eight hours. The resultant reaction solution was cooled, then dissolved in 200 ml of dichloromethane, washed with water and washed again with a dilute aqueous alkali. Subsequently, the reaction product was extracted repeatedly with 1 N hydrochloric acid and the extracted product, upon alkalization, immediately gave rise to precipitation of crystals. The crystals were separated by filtration and dried. The crystalline product was dissolved in hot methyl cyclohexane, freed from insoluble material by decantation and recrystallized. Consequently, there were obtained 30.2 g of γ-(p-formylstyryl)-pyridine crystals having a melting point of 84° to 86.5° C. By the same procedure, but using γ-picoline and the dialdehyde, γ-(p-formylstyryl)-pyridine having a melting point of 111° to 113° C. was obtained.

EXAMPLE 2

In 80 ml of ethyl acetate, 10.0 g of α-(p-formylstyryl)-pyridine and 7.2 g of dimethyl sulfate were dissolved and refluxed under application of heat for five hours. Two hours after the completion of the reaction, the reaction solution was cooled. The reaction product was separated by filtration, washed with ethyl acetate and dried. Consequently, there was obtained 15 g of yellow N-methyl-α-(p-formylstyryl)-pyridinium methosulfate having a melting point of 151° to 154° C.

EXAMPLE 3

In 20 ml of ethanol were hot dissolved 5.00 g of N-methyl-α-picolinium p-toluene-sulfonate and 10.0 g of terephthal dialdehyde. The resultant mixture, after addition thereto of five drops of piperidine, was refluxed for three hours. The resultant reaction solution was cooled, freed from about 10 ml of ethanol through distillation under vacuum, mixed with ethyl acetate to give rise to a yellow precipitate. The precipitate was separated by decantation and washed twice with ethyl acetate. When this separated precipitate was dissolved in hot ethanol and gradually mixed with ethyl acetate, there were precipitated bright yellow crystals. The crystals, when separated by filtration, washed with ethyl acetate and dried, produced 5.57 g of N-methyl-α-(p-formylstyryl)-pyridinium p-toluenesulfonate.

EXAMPLE 4

In 50 ml of methanol were dissolved 50 g of p-hydroxybenzaldehyde and 23 g of potassium hydroxide. The resultant was freed from the solvent through distillation under vacuum and then dried, to produce a potassium salt. This salt was dissolved in 60 ml of N-methylpyrrolidone, mixed with 70 g of chloroacetaldehyde dimethyl acetal and refluxed at 150° C. for 15 hours. The resultant reaction solution was cooled, mixed with 200 ml of dichloromethane, washed three times with water and then washed twice with 50 ml of an aqueous 20 weight % caustic soda solution to extract the unreacted portion of hydroxyaldehyde. The organic layer was washed once with water, dried over anhydrous potassium carbonate and then freed from dichloromethane through distillation under vacuum. When the residual oil was distilled under vacuum, there were obtained N-methyl pyrolidone (bp$_3$ 135° C.) and then p-formylphenoxyacetaldehyde dimethylacetal (bp$_3$ 145° C.). The product obtained through the redistillation totalled 34.2 g.

EXAMPLE 5

In 10 ml of 2-ethoxyethyl alcohol were dissolved 4.88 g of m-hydroxybenzaldehyde and 1.65 g of caustic soda. The resultant solution, after addition thereto of 7.4 g of bromoacetaldehyde dimethylacetal, was refluxed for 20 hours. The resultant reaction solution was cooled, mixed with benzene, washed once with water and then washed with a dilute alkali solution until the hydroxyaldehyde was completely removed. When the benzene solution was desiccated over anhydrous potassium carbonate and then distilled, there was obtained 3.6 g of m-formylphenoxyacetaldehyde dimethyl acetal (bp$_3$ 138° C.). By repeating this procedure faithfully by using o-hydroxybenzaldehyde, there were obtained o-formylphenoxyacetaldehyde dimethylacetal (bp$_5$ 147° C.) and γ-(p-formylphenoxy)-butylaldehyde dimethyl acetal (bp$_3$ 168° C.).

EXAMPLE 6

In 7 ml of methanol were dissolved 1.61 of N-methyl-α-picolinium iodide and 1.70 g of p-formylphenoxyacetaldehyde dimethyl acetal. The resultant mixture, after addition thereto of 0.3 ml of piperidine, was refluxed for four hours. When the reaction solution was cooled, there ensued precipitation of crystals. The crystals were recovered, washed with a small amount of cooled methanol and washed thoroughly with acetone. Thus, there was obtained 2.11 g of 1-methyl-2-{p-(2,2-dimethoxyethoxy)-styryl}-pyridinium iodide having a melting point of 192° to 197° C. By following the same procedure, but using the n-methyl-α-picolinium iodide in combination with m-formylphenoxyacetaldehyde dimethylacetal and n-methyl-γ-picolinium p-tolunesulfonate in combination with p-formylphenoxyacetaldehyde dimethylacetal, as the raw materials, there were respectively obtained 1-methyl-2-{m-(2,2-dimethoxyethoxyl)-styryl}-pyridinium iodide having a melting point of 181° to 186° C., 1-methyl-2-{o-(2,2-dimethoxyethoxy)-styryl}-pyridinium iodide having a melting point of 169° to 173° C., and 1-methyl-4-{p-(2,2-dimethoxyethoxy)-styryl}-pyridinium p-toluenesulfonate having a melting point of 219° to 226° C.

EXAMPLE 7

In 28 ml of water, 2 g of partially saponified polyvinyl alcohol (87% of saponification ratio) having a polymerization degree of 500 was dissolved. In the resultant aqueous solution was dissolved 800 mg of 1-methyl-2-(p-formylstyryl)-pyridinium p-toluenesulfonate. The yellow solution which was formed consequently was shaken at 60° C. for 15 hours in the presence of 1 g of p-toluene sulfonate added thereto. The shaken mixture was introduced dropwise into a large volume of acetone, and the precipitate produced in the acetone was separated by decantation and washed twice with acetone. The washed precipitate was stirred in ethanol containing a small amount of ammonia for 30 minutes, then separated by filtration and dried. Thus, 1.89 g of a polymer was obtained. In its aqueous solution, this polymer showed a maximum absorption at 337 nm. By use of the absorption coefficient of 1-methyl-2-styrylpyridinium p-toluenesulfonate, this polymer was demonstrated to possess 1.80 mol% of styrylpyridinium unit. A film produced from the aqueous solution produced a clear negative image when it was exposed for 30 seconds to the beam from a 450-W high pressure mercury lamp. The sensitivity of the film relative to the sensitivity of the polyvinyl cinnamate having a polymerization degree of 1700 and sensitized with 5-nitroacenaphthene (10 W/W%) (hereinafter referred to as "relative sensitivity") was 2.5.

EXAMPLE 8

In 1 g of an aqueous 10 W/W% solution of 87% saponified polyvinyl alcohol having a polymerization degree of 500, 30 mg of 1-(2-hydroxyethyl)-2-(p-formylstyryl)-pyridinium chloride was dissolved. The resultant mixture was stirred at 70° C. for 12 hours in the presence of 100 mg of p-toluene sulfonic acid added thereto. The resultant reaction solution was introduced dropwise into a large volume of ethanol. The precipitate consequently formed in the solution was separated by filtration, washed with ethanol and dried, to give 92 mg of a product. The content of styrylpyridinium group introduced in the product was 1.50%. The relative sensitivity of the resin was found to be 1.1.

EXAMPLE 9

In 2 g of an aqueous 5 W/W% solution of 87% saponified polyvinyl alcohol having a polymerization degree of 500, 80 mg of 1-methyl-2-(p-formylstyryl)-pyridinium p-toluene-sulfonate was dissolved. In the presence of 100 mg of 80% sulfuric acid added thereto, the resultant mixture was stirred at 60° C. for 15 hours. The resultant reaction solution was poured into a large volume of ethanol, and the precipitate formed consequently was separated four times by decantation and washed with ethanol. The separated precipitate was immersed for 30 minutes in ethanol containing a small amount of ammonia. The resin was separated from the bath through filtration, washed with ethanol and dried. Consequently, there was obtained 107 mg of a product having 0.65 mol% of styrylpyridinium unit. The resin's relative sensitivity was found to be 1.3.

EXAMPLE 10

To 2 g of an aqueous 5 W/W% solution of 87% saponified polyvinyl alcohol having a polymerization degree of 500, 80 mg of 1-methyl-2-(m-formylstyryl)-pyridinium p-toluenesulfonate was added and the resultant mixture was stirred at 75° C. for 15 hours. The resultant reaction solution was poured into a large volume of acetone and then washed through decantation twice with acetone, twice with ethanol and once with ammonia-containing ethanol. Thus, there was obtained 110 mg of a product. By analysis with the ultraviolet absorption spectrometry, the resin was demonstrated to have a styrylpyridinium group content of 1.9 mol%. The film of the resin had a relative sensitivity of 1.5.

EXAMPLE 11

In 5 g of an aqueous 5 W/W% solution of thoroughly saponified polyvinyl alcohol having a polymerization degree of 2000, 80 mg of 1-methyl-2-(p-formylstyryl)-pyridinium p-toluenesulfonate was dissolved. In the presence of 200 mg of p-toluene sulfonic acid added thereto, the resultant mixture was stirred at 60° C. for 15 hours. The reaction solution obtained consequently was poured into a large volume of acetone, giving rise to a precipitate. This precipitate was dried twice with acetone and once with ethanol and dried. Consequently, 263 mg of a polymer was obtained. The resin was found to have a styrylpyridinium group content of 2.10% and a relative sensitivity of 18.

EXAMPLE 12

In 2 g of an aqueous 5 W/W% solution of 87% saponified polyvinyl alcohol having a polymerization degree of 2400, 60 mg of 1-methyl-2-(p-formylstyryl)-pyridinium p-toluenesulfonate was dissolved. The resultant mixture, after addition thereto of 500 mg of p-toluene sulfonic acid, was stirred at 60° C. for 15 hours. The resultant reaction solution was introduced dropwise into a large volume of acetone. The precipitate consequently produced was washed twice with acetone and once with ethanol, then immersed in ammonia-containing ethanol for 30 minutes, separated and dried. Thus, 113 mg of a polymer was obtained. The resin had a styrylpyridinium unit of 2.0 mol%. The film of this resin showed a relative sensitivity of 50.

EXAMPLE 13

In 10 ml of water, 200 mg of 87% saponified polyvinyl alcohol having a polymerization degree of 500 was dissolved. The mixture, after addition thereto of 40 mg of 1-methyl-2-(p-formylstyryl)-pyridinium iodide and 100 mg of 85% phosphoric acid, was stirred at 60° C. for three hours. The reaction solution was immediately poured into a large volume of acetone. The precipitate consequently formed was washed thoroughly three times with methanol and then dried. Thus, 205 mg of a polymer was produced. This resin was found to have a styrylpyridinium unit of 1.7 mol% and a relative sensitivity of 2.0.

EXAMPLE 14

In 2 ml of water, 400 mg of 87% saponified polyvinyl alcohol having a polymerization degree of 500 was dissolved. The mixture, after addition thereto of 40 mg of 1-methyl-4-(p-formylstyryl)-pyridinium p-toluenesulfonate and 0.5 g of 85% phosphoric acid, was stirred at 65° C. for ten hours. The reaction solution was poured into a large volume of acetone. The precipitate consequently produced was washed four times with methanol and then vacuum dried. Thus, 399 mg of a polymer was obtained. This resin was found to have a styrylpyridinium group unit of 0.70 mol% and a relative sensitivity of 0.7.

EXAMPLE 15

In 15 ml of water, 1 g of 87% saponified polyvinyl alcohol having a polymerization degree of 1700 was dissolved. The mixture, after addition thereto of 100 mg of 1-methyl-4-(p-formylstyryl)-pyridinium p-toluenesulfonate and 0.5 g of 85% phosphoric acid, was stirred at 80° C. for eight hours. The reaction solution was poured into a large volume of acetone and a precipitate formed. The precipitate was thoroughly disintegrated and washed three times with methanol. After it was confirmed that the washings no longer assumed a yellow color, the product was vacuum dried. Thus, 0.95 g of a polymer was obtained. Through absorption spectrometry, this resin was shown to possess the maximum absorption at 343 nm and have a styrylpyridinium group content of 1.02%. The resin showed a relative sensitivity of 12. The film prepared from the reaction solution prior to purification showed a relative sensitivity of 7.

EXAMPLE 16

To 10 g of an aqueous 5 W/W% solution of 87% saponified polyvinyl alcohol having a polymerization degree of 1700, 100 mg of 1-methyl-2-(p-formylstyryl)-pyridinium-methosulfate was added. The resultant mixture was thoroughly stirred and mixed with 3 g of 85% phosphoric acid with stirring. Consequently, there was obtained a yellow homogeneous solution. This solution was maintained overnight at 67° C. and then poured into a large volume of acetone. The precipitate consequently formed in the solution was collected. This precipitate was washed twice with ethanol and dissolved in water and reprecipitated in acetone for the purpose of purification. Thus, 0.47 g of a resin was obtained. This resin had a styrylpyridinium unit of 1.20 mol% and a relative sensitivity of 3.0.

EXAMPLE 17

To 10 g of an aqueous 5 W/W% solution of 87% saponified polyvinyl alcohol having a polymerization degree of 500, 30 mg of 1-methyl-2-(p-formylstyryl)-pyridinium-methosulfate was added. The mixture was thoroughly stirred and then mixed with 0.5 ml of 6 N hydrochloric acid with stirring, to produce a yellow homogeneous solution. This solution was maintained at 70° C. for eight hours. The hot solution was poured into a large volume of acetone. The precipitate consequently formed in the solution was washed three times with methanol and then dried. Thus, 482 mg of a resin was obtained. This resin had a styrylpyridinium unit of 0.45 mol% and showed a relative sensitivity of 0.8.

EXAMPLE 18

In 10 g of an aqueous 5 W/W% solution of 87% saponified polyvinyl alcohol having a polymerization degree of 1700, 30 mg of 1-carbamoylmethyl-4-(p-formylstyryl)-pyridinium chloride was dissolved. The mixture, after addition thereto of 1 g of 85% phosphoric acid, was stirred at 50° C. for ten hours. The resultant reaction solution was poured into a large volume of acetone. The precipitate consequently formed therein was washed four times with methanol and vacuum dried. Thus, 0.45 g of a resin was obtained. This resin had a styrylpyridinium unit of 0.52 mol% and showed a relative sensitivity of 4.0.

EXAMPLE 19

In 210 ml of water, 21 g of 87% saponified polyvinyl alcohol having a polymerization degree of 1700 was dissolved by application of heat. The solution was homogeneously mixed with 20 ml of water having dissolved in advance therein 2.1 g of 2-(p-formylstyryl)-pyridine and 3 g of 85% phosphoric acid. The solution was stirred at 70° C. for six hours. The reaction solution had a styrylpyridinium unit of 1.26 mol% based on the polyvinyl alcohol. When this reaction solution was applied in its unmodified form to an aluminum plate and the resultant film was exposed to light and then developed with a weakly acidic aqueous solution, there was obtained a clear negative image. The film's relative sensitivity was found to be 6.7.

EXAMPLE 20

In 7 ml of water, 500 mg of 87% saponified polyvinyl acetate having a polymerization degree of 1700 was added. Then, 187 mg of 1-methyl-4-{p-(2,2-dimethoxyethoxy)-styryl}-pyridinium-methosulfate (see Example 6). The resultant solution, after addition thereto of 0.5 ml of 85% phosphoric acid, was stirred at 60° C. for 15 hours. The reaction solution showed a high degree of sensitivity in itself. It was further processed as follows to afford a resin. The yellow reaction solution was poured into a large volume of acetone to produce a resin in the form of precipitate. The precipitate was thoroughly washed twice with methanol and vacuum dried. Thus, there was obtained 420 mg of resin. The resin, in its aqueous solution, showed maximum absorption at 370 nm. The resin was estimated to have a styrylpyridinium unit of 2.20 mol% on the basis of the ultraviolet absorption spectrum. This resin was converted into an aqueous solution, applied to an aluminum plate and dried, and the resultant film was exposed through a negative image to the beam from a 450-W high pressure mercury lamp and then developed with water. Consequently, there was obtained a clear image. The resin's relative sensitivity was found to be 30.

When the procedure described above was repeated by using the partially saponified polyvinyl acetate and the phosphoric acid in the same amounts as above, except that the amount of the aforementioned pyridinium salt was changed to 97.1 mg in one test run and 49.5 mg in another test run, there were obtained photosensitive polyvinyl alcohol resins having 1.10 mol% and 0.71 mol% respectively of styrylpyridinium unit. These resins were found to have 12 and 9 respectively of relative sensitivity.

EXAMPLE 21

In 6 g of an aqueous 8 weight % solution of 87% saponified polyvinyl acetate (having a polymerization degree of 1700), 63 mg of 1-methyl-2-{o-(2,2-dimethoxyethoxy)-styryl}-pyridinium iodide was added. The resultant mixture, after addition thereto of 150 mg of p-toluene sulfonic acid, was treated at 60° C. for 15 hours to induce a reaction. The yellow reaction solution consequently produced was poured into a large volume of acetone. The resin which occurred in the form of precipitate was washed twice with methanol and then dried under vacuum. Thus, 409 mg of purified resin was obtained. The aqueous solution of this resin showed the maximum absorption at 356 nm. On the basis of the absorption coefficient of the pyridinium salt used as the raw material, the resin was estimated to contain 1.43 mol% of styrylpyridinium group. When tested by the gray scale method, this resin showed a relative sensitivity of 2.7. When the procedure described above was repeated by using 33 mg of the pyridinium salt, there was obtained a resin having a styryl-pyridinium unit of 0.81 mol%. The relative sensitivity of this resin was 0.6.

EXAMPLE 22

In 6 g of an aqueous 8 weight % solution of 87% saponified polyvinyl acetate (having a polymerization degree of 1700), 60.5 mg of 1-methyl-2-{m-(2,2-dimethoxyethoxy)-styryl}-pyridinium iodide was homogeneously dissolved. The solution, after addition thereto of 150 mg of p-toluene sulfonic acid, was stirred at 60° C. for 15 hours. The reaction solution was poured into a large volume of acetone. The resin consequently educed in the solution was washed twice with methanol and then dried under vacuum. Thus, there was obtained 420 mg of a purified resin. The aqueous solution of this resin showed the maximum absorption at 338 nm. On the basis of the absorption spectrum, the resin was estimated to have a styrylpyridinium content of 1.43%. The resin's relative sensitivity was 7.0. When the procedure described above was repeated by using 32.8 mg of the aformentioned pyridinium salt, there was obtained a resin having a styrylpyridinium unit of 0.82 mol%. The relative sensitivity of this resin was 2.4.

EXAMPLE 23

In 6 g of an aqueous 8 weight % solution of 87% saponified polyvinyl acetate (having a polymerization degree of 1700), 61.4 mg of 1-methyl-2-{p-(2,2-dimethoxyethoxy)-styryl}-pyridinium iodide was dissolved. The solution was mixed with 150 mg of p-toluene sulfonic acid to produce a homogeneous solution, which was treated at 60° C. for 15 hours to induce a reaction. The yellow reaction solution thus formed was poured into a large volume of acetone. The resin which occurred consequently was washed twice with methanol and then dried under vacuum. Thus there was obtained 420 mg of a purified resin. The aqueous solution of this resin showed the maximum absorption at 361 nm. On the basis of the absorption spectrum, this resin was estimated to have a styrylpyridinium unit of 1.27 mol%. This resin had a relative sensitivity of 9.0. When the procedure described above was repeated by using 33.7 mg of the aforementioned pyridinium salt, there was obtained a resin having a styrylpyridinium unit of 0.75 mol%. It showed a relative of 4.0.

EXAMPLE 24

In 6 g of an aqueous 8 weight % solution of 87% saponified polyvinyl acetate (having a polymerization degree of 1700), 65.0 mg of 1-methyl-2-{p-(4,4-dimethoxybutoxy)-styryl}-pyridinium iodide obtained from N-methyl-α-picolinium iodide and γ-(p-formylphenoxy)-butylaldehyde dimethylacetal by the procedure of Example 6 was homogeneously dissolved. The resultant solution, after addition thereto of 150 mg of p-toluene sulfonic acid, was treated at 60° C. for 15 hours to induce a reaction. The yellow reaction solution was poured into a large volume of acetone. The resin consequently formed was washed twice with methanol and then dried under vacuum. Thus, there was obtained 430 mg of a purified resin. This resin, in its aqueous solution, showed the maximum absorption at 361 nm. On the basis of the absorption spectrum, the resin was estimated to have a styrylpyridinium unit of 1.05 mol%. The resin's relative sensitivity was 3.2

What is claimed is:

1. A photosensitive resin, comprising: a polyvinyl alcohol or a partially hydrolyzed polyvinyl acetate polymeric backbone containing units of the formula:

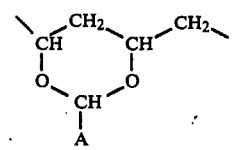

wherein A is a photosensitive substituent selected from the group consisting of
(A) a group of the generic formula:

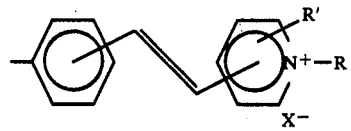

wherein, R represents one member selected from the class consisting of a hydrogen atom, alkyl groups and lower hydroxyalkyl groups, R' one member selected from the class consisting of a hydrogen atom and alkyl groups and
(B) a group of the generic formula:

wherein, $R_1$ represents one member selected from the class consisting of a hydrogen atom, alkyl groups and aralkyl groups, $R_2$ one member selected from the class consisting of a hydrogen atom and alkyl groups, n an integer having a value between 1 and 6 inclusive and $X^-$ a strongly acidic ion, and wherein the molar ratio of said photosensitive substituent to the vinyl alcohol or vinyl acetate units of said polyvinyl alcohol or partially hydrolyzed polyvinyl acetate polymeric backbone ranges from 0.5:99.5 to 10:90, said polyvinyl alcohol or partially hydrolyzed polyvinyl acetate polymeric backbone having a degree of polymerization of 400 to 3000.

2. The photosensitive resin according to claim 1, wherein $X^-$ represents one member selected from the group consisting of halogen ions, sulfate ion, phosphate ion and p-toluene sulfonate ion.

3. The photosensitive resin according to claim 1, wherein the polymerization degree of the polyvinyl alcohol falls in the range of from 400 to 3000.

4. A method for the manufacture of a photosensitive resin comprising a polyvinyl alcohol or a partially hydrolyzed polyvinyl acetate polymeric backbone containing units of the formula:

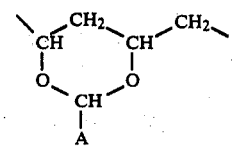

wherein A is a photosensitive substituent selected from the group consisting of
(A) a group of the generic formula:

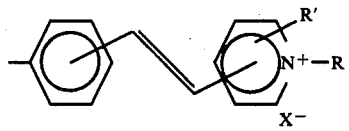

wherein, R represents one member selected from the class consisting of a hydrogen atom, alkyl groups and lower hydroxyalkyl groups, R' one member selected from the class consisting of a hydrogen and alkyl groups and $X^-$ a strongly acidic ion, and
(B) a group of the generic formula:

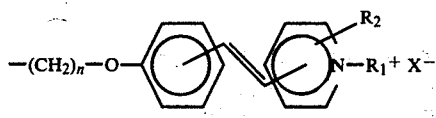

wherein, $R_1$ represents one member selected from the class consisting of a hydrogen atom, alkyl groups and aralkyl groups, $R_2$ one member selected from the class consisting of a hydrogen atom and alkyl groups, n an integer having a value between 1 and 6 inclusive and $X^-$ a strongly acidic ion, which method comprises: reacting one member selected from the group consisting of polyvinyl alcohols and partially saponified polyvinyl acetates in the presence of an acid catalyst with a photosensitive compound selected from the group consisting of
(1) styrylpyridinium salts possessing a formyl group and represented by the generic formula:

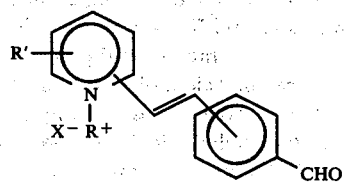

wherein, R represents one member selected from the class consisting of a hydrogen atom, alkyl groups and lower hydroxyalkyl groups, R' one member selected from the class consisting of a hydrogen and alkyl groups and $X^-$ a strongly acidic ion, and
(2) styrylpyridinium salts possessing an acetal group and represented by the generic formula:

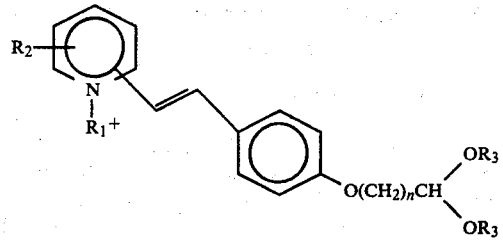

wherein, $R_1$ represents one member selected from the class consisting of a hydrogen atom, alkyl groups and aralkyl groups, $R_2$ one member selected from the class consisting of a hydrogen atom and alkyl groups, two $R_3$'s one member selected from the class consisting of an alkyl group and a phenyl group in their respective forms and in a combined form an alkenyl group, n an integer having a value between 1 and 6 inclusive and $X^-$ a strongly acidic ion.

5. The method according to claim 4, wherein $X^-$ represents one member selected from the group consisting of halogen ions, sulfate ion, phosphate ion and p-toluene sulfonate ion.

6. The method according to claim 4, wherein the styrylpyridinium salt possessing a formyl group is used in a proportion of from 0.3 to 20 mol% based on one vinyl alcohol unit selected from the group consisting of polyvinyl alcohols and partially saponified polyvinyl acetates.

7. The method according to claim 4, wherein the styrylpyridinium salt possessing an acetal group is used in a proportion of from 0.3 to b 20 mol% based on one vinyl alcohol unit selected from the group consisting of polyvinyl alcohols and partially saponified polyvinyl acetates.

8. The method according to claim 4, wherein said acid catalyst is hydrochloric acid, sulfuric acid, phosphoric acid, perchloric acid, hydroborofluoric acid, methanesulfonic acid or p-toluenesulfonic acid.

9. The method according to claim 4, wherein said reaction is conducted at a temperature of room temperature to 100° C.

10. The method according to claim 4, wherein the polyvinyl alcohol or a partially hydrolyzed polyvinyl acetate polymeric backbone is present in said reaction in a concentration of 2 to 20 W/W%.

* * * * *